(12) United States Patent
Horiike et al.

(10) Patent No.: US 8,029,446 B2
(45) Date of Patent: Oct. 4, 2011

(54) ULTRASONIC IMAGING SYSTEM AND IMAGING METHOD

(75) Inventors: Toyokazu Horiike, Shizuoka (JP); Hiroyuki Yagami, Shizuoka (JP); Kazuhiro Hirota, Kanagawa (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 1047 days.

(21) Appl. No.: 11/089,330

(22) Filed: Mar. 25, 2005

(65) Prior Publication Data
US 2006/0241484 A1 Oct. 26, 2006

(30) Foreign Application Priority Data
Mar. 25, 2004 (JP) ................................. 2004-090019

(51) Int. Cl.
*A61B 8/14* (2006.01)
(52) U.S. Cl. .................. 600/463; 600/467; 600/549
(58) Field of Classification Search .................. 600/407, 600/437–438, 443, 473–475, 549, 462–467, 600/459; 374/141–142, 148, 183
See application file for complete search history.

(56) References Cited

U.S. PATENT DOCUMENTS

| | | | | |
|---|---|---|---|---|
| 5,469,852 A * | 11/1995 | Nakamura et al. | ............. | 600/463 |
| 5,596,995 A * | 1/1997 | Sherman et al. | ............. | 600/549 |
| 5,855,563 A * | 1/1999 | Kaplan et al. | ................. | 604/509 |
| 5,924,997 A * | 7/1999 | Campbell | ..................... | 600/549 |
| 5,935,075 A | 8/1999 | Casscells et al. | | |
| 6,245,026 B1 * | 6/2001 | Campbell et al. | ............. | 600/549 |
| 6,290,675 B1 | 9/2001 | Vujanic et al. | | |
| 6,475,159 B1 * | 11/2002 | Casscells et al. | ............. | 600/549 |
| 6,514,214 B2 * | 2/2003 | Kokate et al. | ................. | 600/549 |
| 6,615,071 B1 | 9/2003 | Casscells, III et al. | | |
| 6,763,261 B2 | 7/2004 | Casscells, III et al. | | |
| 6,939,313 B2 * | 9/2005 | Saadat et al. | .................. | 600/587 |
| 6,949,072 B2 * | 9/2005 | Furnish et al. | ................ | 600/466 |
| 2002/0115931 A1 * | 8/2002 | Strauss et al. | ................. | 600/420 |
| 2003/0199747 A1 * | 10/2003 | Michlitsch et al. | ........... | 600/407 |
| 2003/0199767 A1 * | 10/2003 | Cespedes et al. | ............. | 600/473 |
| 2003/0236443 A1 * | 12/2003 | Cespedes et al. | .............. | 600/29 |
| 2006/0173318 A1 * | 8/2006 | Sathyanarayan | ............. | 600/437 |

FOREIGN PATENT DOCUMENTS

| | | |
|---|---|---|
| JP | 02-252445 A | 10/1990 |
| JP | 02-289238 A | 11/1990 |
| JP | 04-138147 | 5/1992 |
| JP | 7-38852 | 5/1995 |

(Continued)

*Primary Examiner* — Francis Jaworski
(74) *Attorney, Agent, or Firm* — Buchanan Ingersoll & Rooney PC (57) ABSTRACT

An ultrasonic imaging system includes an imaging catheter and an imaging apparatus. The imaging catheter has an insert for being inserted into a blood vessel, a transducer disposed in the insert, and at least one temperature sensor disposed in the insert. The temperature sensor measures the intravascular temperature in a radial direction of the blood vessel and rotates to measure an intravascular temperature distribution in a transverse cross section of the blood vessel. The diagnostic imaging apparatus has an ultrasonic signal receiver for receiving an ultrasonic signal measured by the transducer, a temperature signal receiver for receiving an intravascular temperature signal measured by the temperature sensor, and an image constructing unit for constructing an image to be displayed from a tomographic vascular image generated from the ultrasonic signal and intravascular temperature information generated from the intravascular temperature signal, in relation to positional information of the ultrasonic signal and the intravascular temperature signal.

16 Claims, 9 Drawing Sheets

FOREIGN PATENT DOCUMENTS

| | | |
|---|---|---|
| JP | 2000-229083 A | 8/2000 |
| JP | 2002-136537 A | 5/2002 |
| JP | 2003-247964 A | 9/2003 |
| JP | 2004-085391 A | 3/2004 |
| JP | 2005-066142 A | 3/2005 |
| WO | WO 03/088817 | 10/2003 |

* cited by examiner

ULTRASONIC IMAGING SYSTEM AND IMAGING METHOD

BACKGROUND OF THE INVENTION

1. Field of the Invention

The present invention relates to an ultrasonic imaging system. The system is comprised of an ultrasonic imaging catheter (an ultrasonic catheter) and a diagnostic imaging apparatus for employing information obtained by the catheter for diagnostic purposes, and more particularly to an ultrasonic catheter for being inserted into a blood vessel in a living body to obtain information such as an ultrasonic image. The diagnostic imaging apparatus functions to obtain an intravascular image from information obtained by an ultrasonic catheter.

2. Description of the Related Art

Ultrasonic diagnostic imaging apparatus for use in body cavities generally have an ultrasonic catheter for scanning a body vessel such as a blood vessel or a vessel.

Figure 1:
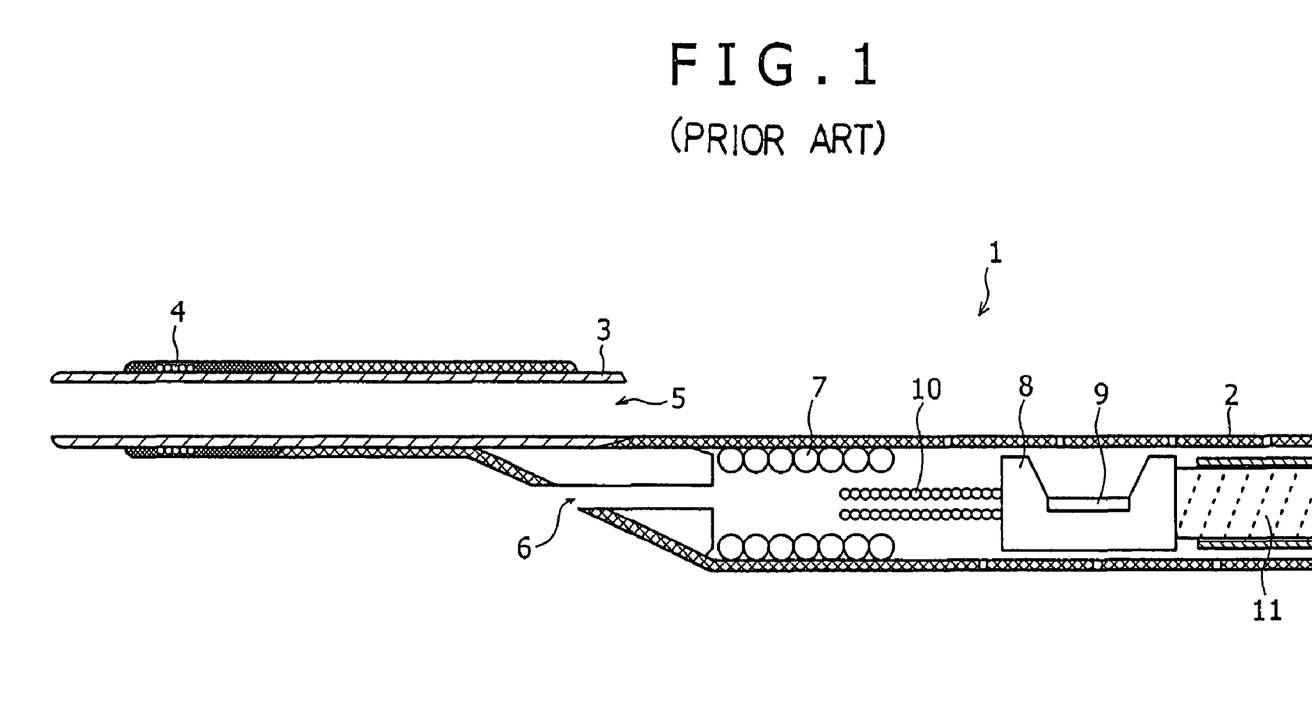
FIG. 1 is a cross-sectional view of a distal end portion of a prior art ultrasonic catheter.

FIG. 1 of the accompanying drawings shows a structure of a distal end portion 1 of such a general ultrasonic catheter. As shown in FIG. 1, the ultrasonic catheter has a catheter tube 2 housing an imaging core therein. The distal end portion 1 is guided by a guide wire (not shown) and inserted into a blood vessel in a living body. The distal end portion 1 has a guide wire lumen tube 3 which has a lumen 5 defined therethrough to receive the guide wire. The guide wire extends through the lumen 5 and guides the ultrasonic catheter in the blood vessel. An X-ray marker 4 made of gold, platinum, or the like is mounted on the tip end of the guide wire lumen 3. The X-ray marker 4 gives a visual indication as to the location of the ultrasonic catheter 1 in the living body in an X-ray radioscopic image.

The ultrasonic catheter also has a priming through hole 6 defined in the distal end portion thereof for removing air from the catheter tube 2 when the catheter tube 2 is filled up with a normal saline solution. The catheter tube 2 houses therein an X-ray marker 7 in the form of a metal coil. The X-ray marker 7 also serves as a stiffener for preventing the ultrasonic catheter from being bent.

A transducer housing 8 disposed in the catheter tube 2 accommodates an ultrasonic transducer 9 therein. A coil 10 is mounted on the tip end of the transducer housing 8 for stabilizing the rotation of the transducer housing 8 when a drive shaft 11 coupled to the transducer housing 8 is rotated by a motor (not shown). The drive shaft 11 is connected to the motor and houses signal lines therein. A coil is wound around the outer surface of the drive shaft 11.

While the drive shaft 11 is being rotated by the motor, the ultrasonic transducer 9 emits and receives ultrasonic waves reflected from the inner wall of the blood vessel in all directions (360° for generating a tomographic image of the blood vessel.

Japanese patent publication No. Hei 7-38852 discloses an ultrasonic probe for sending and receiving ultrasonic waves to acquire a tomographic image of the blood vessel, and introducing the blood from the blood vessel and measuring the temperature of the introduced blood with a temperature sensor. That disclosed ultrasonic probe can detect the temperature of the blood, as well as a tomographic image of the blood vessel like the ultrasonic catheter shown in FIG. 1, for diagnostic purposes.

The distal end portion 1 of the ultrasonic catheter shown in FIG. 1 has only the ultrasonic transducer 9 and is unable to detect the temperature in the blood vessel in a particular location in the living body.

The ultrasonic probe disclosed in Japanese patent publication No. Hei 7-38852 suggests that an ultrasonic tomographic image is displayed on a display unit such as a display monitor or the like. However, it fails to disclose anything about how the temperature information of the blood that is measured by the temperature sensor is used, and about how the temperature information is visually presented. It can only be guessed from the disclosed ultrasonic probe that a numerical value of the temperature information may be displayed together with the ultrasonic tomographic image.

Furthermore, the above two conventional devices suffer the following disadvantages: An intravascular ultrasonic device will be described by way of example. The intravascular ultrasonic device is used to observe the nature of a blood vessel or a blood vessel lumen or the form of an arterial sclerosis in a constricted area which is responsible for a cardiac infarction or the like, and to select an appropriate therapy. The intravascular ultrasonic device is also used to perform a chronological observation of how the arterial sclerosis develops, whether the blood vessel is constricted again, or whether the diameter of the blood vessel changes. The observation is merely the acquisition of information about a plaque that has already been formed. The above analysis applies to the above two conventional devices.

Attempts have been made in recent years to use the intravascular ultrasonic device to measure the intravascular temperature or the temperature of an arteriosclerotic plaque to predict the possibility of an arterial sclerosis. It has been reported that when an arteriosclerotic plaque, though not clearly confirmed by an image, is formed in an arterial coronaria, the intravascular temperature is $0.11\pm0.11°$ C. higher than the normal intravascular temperature when the patient is suffering stable angina, $0.68\pm0.35°$ C. higher than the normal intravascular temperature when the patient is suffering unstable angina, and $1.47\pm0.69°$ C. higher than the normal intravascular temperature when the patient is suffering acute myocardial infarction.

It has also been reported that the temperature of a plaque in a carotid artery, or the temperature in a carotid artery if there is a danger of the formation of a plaque, is 0.4 to $2.2°$ C. higher than the normal intravascular temperature.

An intravascular ultrasonic diagnostic imaging apparatus has a catheter with an ultrasonic transducer incorporated therein. The catheter is inserted into a blood vessel, and the ultrasonic transducer in the catheter is rotated to perform radial scanning on the blood vessel. Based on reflected ultrasonic waves, the intravascular ultrasonic diagnostic imaging apparatus displays a tomographic image of the blood vessel on a display monitor.

An intravascular temperature may be measured by a thermodilution catheter though the thermodilution catheter is originally used for other purpose.

The above two conventional devices need to produce an ultrasonic intravascular tomographic image and measure a temperature separately. Therefore it cannot accurately identify where each of the temperature data is measured in the blood vessel or where there is the plaque because the location where the temperature is measured cannot be specified.

SUMMARY OF THE INVENTION

It is an object of the present invention to provide an ultrasonic imaging system which is capable of simultaneously generating an intravascular tomographic image and measuring an intravascular temperature at a particular location in a living body, and of identifying a measured location in a living body, and an ultrasonic intravascular diagnostic imaging apparatus which is capable of simultaneously visually displaying a generated tomographic image and a measured intravascular temperature.

To achieve the above object, there is provided in accordance with the present invention an ultrasonic imaging system comprising an ultrasonic catheter including an insert for being inserted into a blood vessel, a transducer disposed in the insert, and at least one temperature sensor disposed in the insert, wherein said transducer and said temperature sensor scan the blood vessel in a direction which is perpendicular or parallel to a longitudinal axis of the blood vessel, and said transducer provides a tomographic vascular image of the blood vessel, and said temperature sensor measures an intravascular temperature distribution in the blood vessel.

In the ultrasonic catheter, the temperature sensor may be disposed in the same position as the transducer in a longitudinal direction of the insert.

In the ultrasonic catheter, said transducer has a front side which sends and/or receives an ultrasonic signal and a rear side, and said temperature sensor is mounted a position of the rear side of said transducer.

The ultrasonic catheter may further include a guide wire lumen and a priming hole defined in a junction between the guide wire lumen and a distal end portion of the ultrasonic catheter.

To achieve the above object, in accordance with the present invention, there is also provided a diagnostic imaging system including an ultrasonic catheter having an insert for being inserted into a blood vessel, a transducer disposed in the insert and at least one temperature sensor disposed in the insert for detecting an intravascular temperature, and a diagnostic imaging apparatus including an ultrasonic signal receiver for receiving an ultrasonic signal measured by the transducer, a temperature signal receiver for receiving an intravascular temperature signal measured by the temperature sensor, and an image constructing unit for constructing an image to be displayed from a tomographic vascular image generated from the ultrasonic signal and intravascular temperature information generated from the intravascular temperature signal, in relation to positional information of the ultrasonic signal and the intravascular temperature signal.

The diagnostic imaging apparatus may further include a display unit for displaying the intravascular temperature information divided in differently colored segments, together with the tomographic vascular image.

In the diagnostic imaging apparatus, the temperature sensor may be disposed in the same position as the transducer in a longitudinal direction of the insert.

In the diagnostic imaging apparatus, the display unit may display a pattern diagram of the blood vessel having a plurality of divided regions with an average value of said intravascular temperature information in association with each of said divided regions.

In the diagnostic imaging apparatus, the display unit may display the intravascular temperature information and the tomographic vascular image in superimposed relation to each other.

In the diagnostic imaging apparatus, the temperature sensor and the transducer may be translated in the insert about a longitudinal axis of the blood vessel, and the ultrasonic signal receiver and the temperature signal receiver may receive an ultrasonic signal representative of an intravascular ultrasonic longitudinal tomographic image and an intravascular temperature signal representative of intravascular longitudinal temperature information, respectively. The temperature sensor and the transducer are being moved, and wherein the display unit simultaneously displays the intravascular ultrasonic longitudinal tomographic image and the intravascular longitudinal temperature information in synchronism with the movement of the temperature sensor and the transducer.

In diagnostic imaging apparatus, the display unit may display the intravascular ultrasonic longitudinal tomographic image and the intravascular longitudinal temperature information in superimposed relation to each other.

The ultrasonic catheter is capable of simultaneously generating an intravascular tomographic image and measuring an intravascular temperature at a particular location in a living body, and of identifying a measured location in a living body. The ultrasonic intravascular diagnostic imaging apparatus has such an ultrasonic catheter and is capable of simultaneously visually displaying a generated tomographic image and a measured intravascular temperature.

The above and other objects, features, and advantages of the present invention will become apparent from the following description when taken in conjunction with the accompanying drawings which illustrate preferred embodiments of the present invention by way of example.

DETAILED DESCRIPTION OF THE PREFERRED EMBODIMENTS

Figure 2:
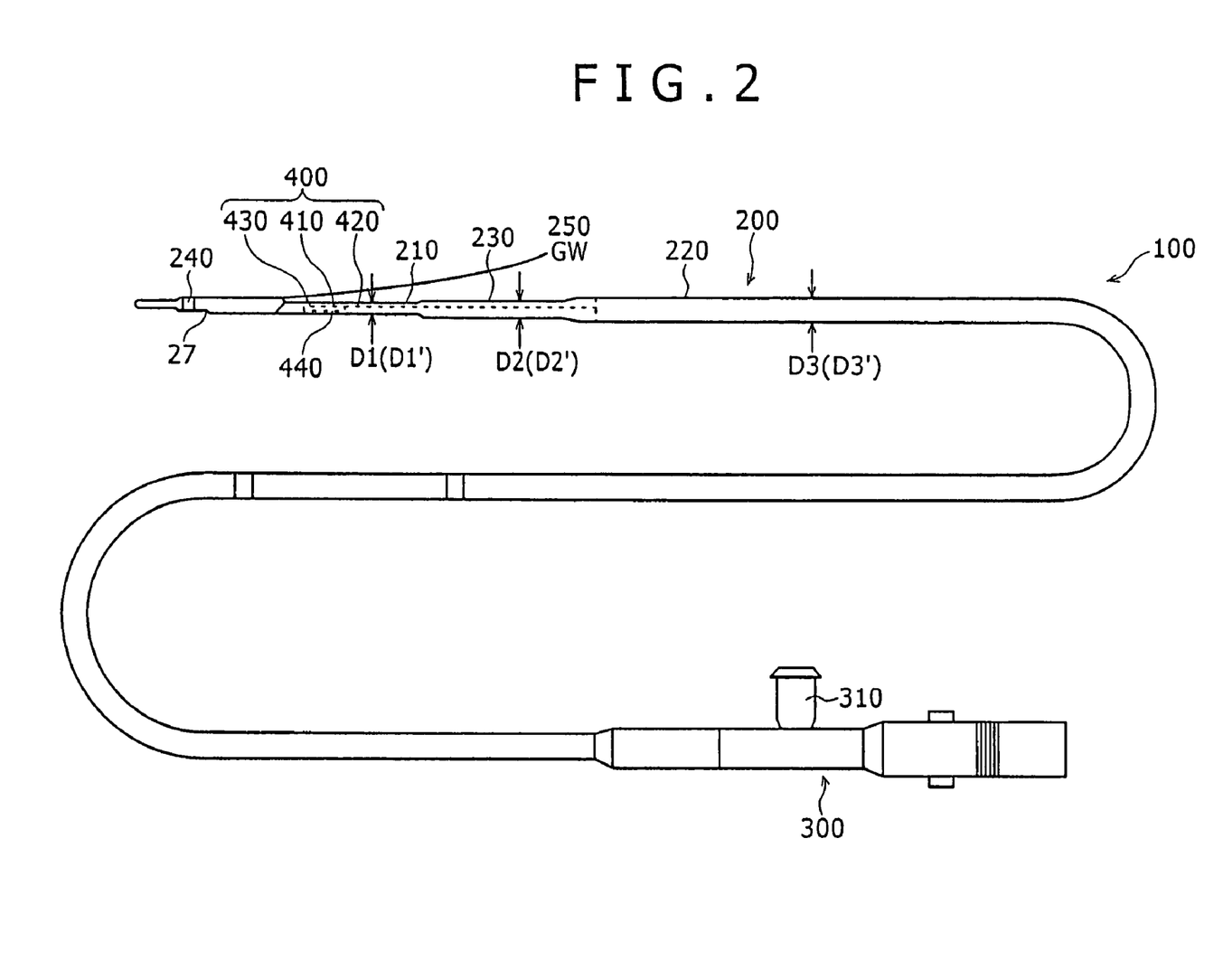
FIG. 2 is a view showing an entire ultrasonic catheter according to the present invention.

FIG. 2 shows an entire ultrasonic catheter 100 according to the present invention.

First Embodiment

As shown in FIG. 2, the ultrasonic catheter 100 includes a sheath 200 serving as an insert to be inserted into a blood vessel and a hub 300 to be manually handled by the user. The hub 300 is positioned at a proximal end of the sheath 200 and not inserted into the blood vessel.

The sheath 200 has a sheath distal end portion 210 (see FIG. 3), a tubular sheath body 220, and an intermediate sheath portion 230. The sheath distal end portion 210 and the sheath body 220 are interconnected by the intermediate sheath portion 230. The sheath body 220 is connected to the hub 300.

The sheath distal end portion 210 has an X-ray marker 240 for giving a visual indication as to the location of the ultrasonic catheter 100 in the living body in an X-ray radioscopic image when the ultrasonic catheter 100 inserted into a blood vessel. The sheath distal end portion 210 also has a guide wire lumen for the passage of a guide wire (GW) 250 therethrough. The guide wire 250 is inserted in the blood vessel in advance and used to guide the ultrasonic catheter 100 to a desired region in the living body. The ultrasonic catheter 100 is guided to the desired region by the guide wire 250 that extends through the guide wire lumen in the sheath distal end portion 210.

The sheath body 220 is connected to the intermediate sheath portion 230 and the hub 300. The sheath distal end portion 210 has an outside diameter D1, the intermediate sheath portion 230 has an outside diameter D2, and the sheath body 220 has an outside diameter D3. These outside diameters D1, D2, D3 are related to each other by D1<D2<D3. For example, the outside diameter D1 is 0.80 mm, the outside diameter D2 is 0.87 mm, and the outside diameter D3 is in the range from 1.04 to 1.06 mm.

Since the wall thickness of the sheath 200 is constant from sheath distal end portion 210 to the sheath body 220, the sheath distal end portion 210, the intermediate sheath portion 230, and the sheath body 220 have respective inside diameters D1', D2', D3' which are related to each other by D1'<D2'<D3'.

An imaging core 400 is housed in the sheath 200. The imaging core 400 includes: (i) a transducer unit 410 serving as an ultrasonic transducer for sending ultrasonic waves to a blood vessel tissue and receiving ultrasonic waves reflected from the blood vessel tissue, (ii) a temperature sensor 440 for detecting an intravascular temperature in the living body, (iii) a drive shaft 420 for rotating and translating the transducer unit 410 and the temperature sensor 440 which are mounted on a tip end thereof, and (iv) a metal coil 430 associated with the transducer unit 410. The imaging core 400 is rotatable and translatable about the sheath 200. The transducer unit 410 emits ultrasonic waves into a region of the living body and receives reflected ultrasonic waves to generate an ultrasonic tomographic image of the region. The signal corresponding to the temperature of the blood vessel wall which a surface of the temperature sensor 440 has turned towards can be acquired from the temperature sensor 440.

The sheath distal end portion 210 according to the present invention will be described in specific detail below with reference to FIG. 3.

Figure 3:
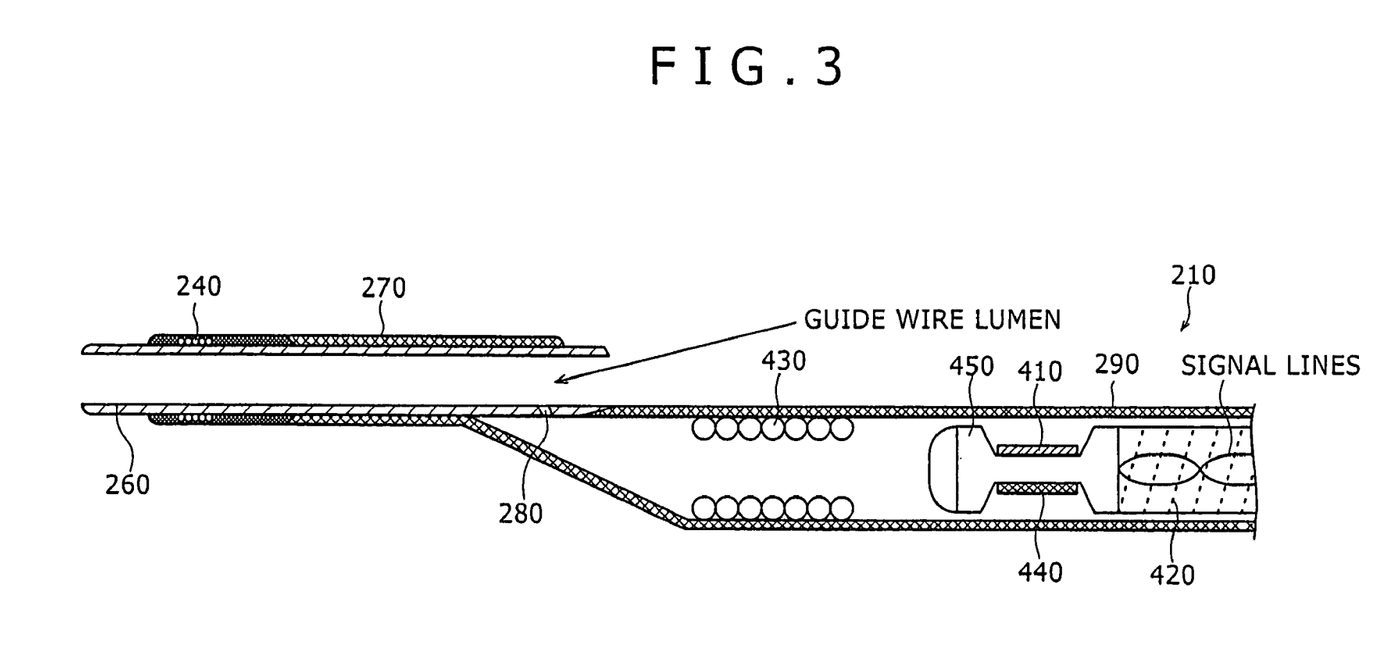
FIG. 3 is a cross-sectional view of a sheath distal end portion according to a first embodiment of the ultrasonic catheter according to the present invention.

As shown in FIG. 3, the sheath distal end portion 210 has a guide wire insertion tube 270 which provides a guide wire lumen therein. The guide wire 250 has its rear end inserted into the guide wire insertion tube 270, and extends through the guide wire insertion tube 270. The guide wire 250 thus inserted guides the ultrasonic catheter 100 to a desired position in the living body.

In FIG. 3, the imaging core 400 includes the transducer unit 410 for sending and receiving ultrasonic waves and the temperature sensor 440 for detecting temperatures in body cavities (blood vessels and vessels). The transducer unit 410 and the temperature sensor 440 have a size of about 1 mm each, and are disposed in a single housing 450. The transducer unit 410 has a front side which sends and receives an ultrasonic signal, and a rear side. The temperature sensor 440 is mounted in the housing 450 at the 180-degree opposite side (rear side) of the transducer unit 410. The imaging core 400 may have one or more temperature sensors 440 which may be positioned alongside of the transducer unit 410 or juxtaposed, rather than behind the transducer unit 410. The imaging core 400 may also have a plurality of transducer units 410.

When the drive shaft 420 transmits rotational power from a motor (not shown), the transducer unit 410 and the temperature sensor 440 are rotated thereby to observe a desired region in a body cavity, such as a blood vessel or a vesseL in an angular range of 360°. The transducer unit 410 for sending and receiving ultrasonic waves and the temperature sensor 440 for detecting temperatures in blood vessel are disposed in the sheath distal end portion 210 for simultaneously acquiring both information for generating an ultrasonic tomographic image and temperature information in the blood vessel. Here, the temperature detected by the temperature sensor 440 is a temperature of a blood vessel wall temperature that transmits the blood, and the temperature of the wall of the catheter sheath tube 290.

More specifically, the transducer unit 410 and the temperature sensor 440 are disposed in the same location with respect to the longitudinal direction of the imaging core 400, i.e., the scanning direction of the ultrasonic catheter 100. In FIG. 3, the transducer unit 410 and the temperature sensor 440 are disposed in confronting relation to each other along the longitudinal direction of the imaging core 400. If a plurality of temperature sensors are employed, the transducer unit 410 is also disposed in the same location as the temperature sensors with respect to the longitudinal direction of the imaging core 400. According to this layout, an ultrasonic tomographic image and temperature information of one location in the living body can simultaneously be acquired. Therefore, the image information and the temperature information can easily be combined into a combined image when both are displayed on a display screen, as described later.

If the transducer unit 410 and the temperature sensor 440 were instead disposed in different respective locations with respect to the longitudinal direction of the imaging core 400, then it would be necessary to calculate which temperature information corresponds to which ultrasonic tomographic image from the distances up to the transducer unit 410 and the temperature sensor 440 in order to synchronize the ultrasonic tomographic image and the temperature information with each other. However, it is highly difficult to associated these two data accurately with each other. Specifically, it is difficult to synchronize these two data accurately with each other because movement of the imaging core 400 or the catheter in the living body affects the accuracy of the traveled distance that is detected. For example, when the imaging core 400 or the catheter is pulled 5 mm from outside of the living body, it is not certain whether the transducer and the temperature sensor move equally 5 mm within the living body. Since the imaging core 400 or the catheter is usually inserted through an arm or a thigh of the patient, it is bent many times before it reaches the heart. Therefore, no one is sure as to whether the transducer and the sensor move equally 5 mm within the living body. In addition, after a certain region such as a region with a plaque is detected by an IVUS (IntraVascular Ultra-Sonic) image, the imaging core 400 or the catheter is moved to cause the temperature sensor to reach that region. However, it is very difficult to accurately move the imaging core 400 or the catheter. These problems can be solved by simultaneously acquiring the ultrasonic tomographic image and the temperature information in accordance with the present invention.

Moreover, inasmuch as the transducer unit 410 and the temperature sensor 440 are disposed in the same location with respect to the longitudinal direction of the imaging core 400, the imaging core 400 itself can be reduced in size. With the imaging core 400 reduced in size, the ultrasonic catheter 100 may be made thinner for easy insertion through bent passages.

The metal coil 430 is disposed in a distal end portion of the imaging core 400. The metal coil 430 is used as an X-ray marker and also serves to prevent a catheter tube 290 made of polyethylene, for example, whose outside diameter is 1.0 mm and inside diameter is 0.85 mm, from being bent.

The sheath distal end portion 210 has a priming hole 280. When an ultrasonic transfer medium such as a normal saline solution is introduced from an inlet port 310 (see FIG. 2) into the catheter tube 290, an excess of the ultrasonic transfer medium is removed from the priming hole 280 so that the space around imaging core 400 is filled up with the ultrasonic transfer medium. According to the present embodiment, the priming hole 280 is much narrower than the conventional priming hole for minimizing any backward flow of the blood into the catheter tube 290. The ultrasonic transfer medium is primed through the priming hole 280 in each cycle of producing an ultrasonic tomographic image and measuring the temperature. Therefore, bubbles trapped around the transducer unit 410 can be removed for more accurate measurement. Though the temperature sharply drops when the ultrasonic transfer medium is primed, the temperature immediately rises up to the normal level.

Figure 4:
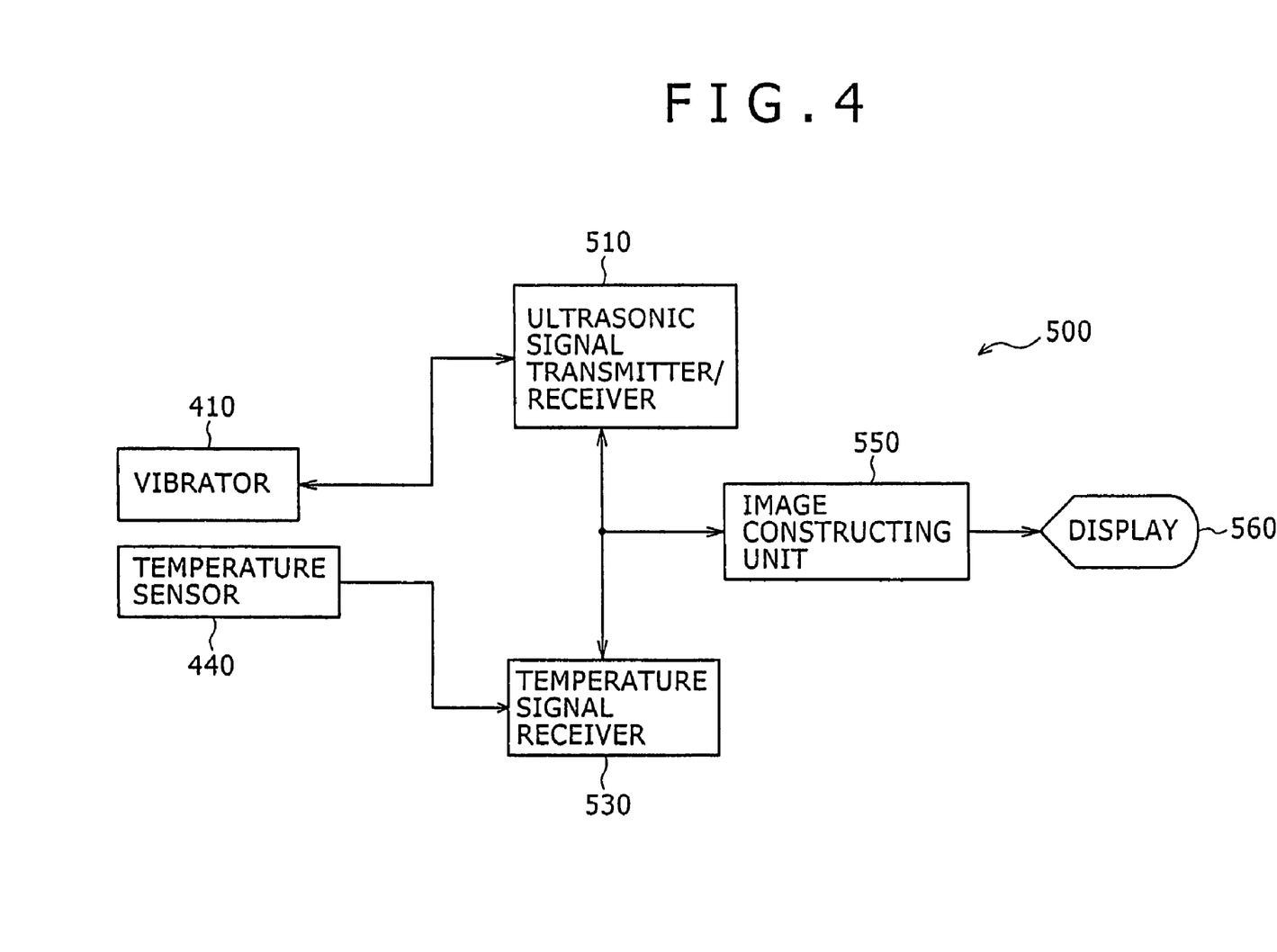
FIG. 4 is a block diagram of an ultrasonic intravascular diagnostic imaging apparatus according to the present invention.

FIG. 4 shows in block form an intravascular ultrasonic diagnostic imaging apparatus 500 for processing ultrasonic data and temperature data detected by the ultrasonic catheter 100.

As shown in FIG. 4, an ultrasonic signal received by the transducer unit 410 is amplified, logarithmically converted, and detected by an ultrasonic signal transmitter/receiver 510, and then sent to an image constructing unit 550. The image constructing unit 550 converts the ultrasonic signal into a digital ultrasonic signal and constructs an image from the digital ultrasonic signal. A display unit 560 displays the image constructed by the image constructing unit 550.

A temperature signal detected by the temperature sensor 440 is amplified, corrected, and converted in voltage by a temperature signal receiver 530, and then sent to the image constructing unit 550. The image constructing unit 550 converts the temperature represented by the temperature signal and constructs a temperature image from the temperature signal. The display unit 560 displays the temperature image constructed by the image constructing unit 550. The ultrasonic signal and the temperature signal from the ultrasonic catheter 100 are collected as data while the imaging core 400 is rotated by the non-illustrated motor.

Figure 5:
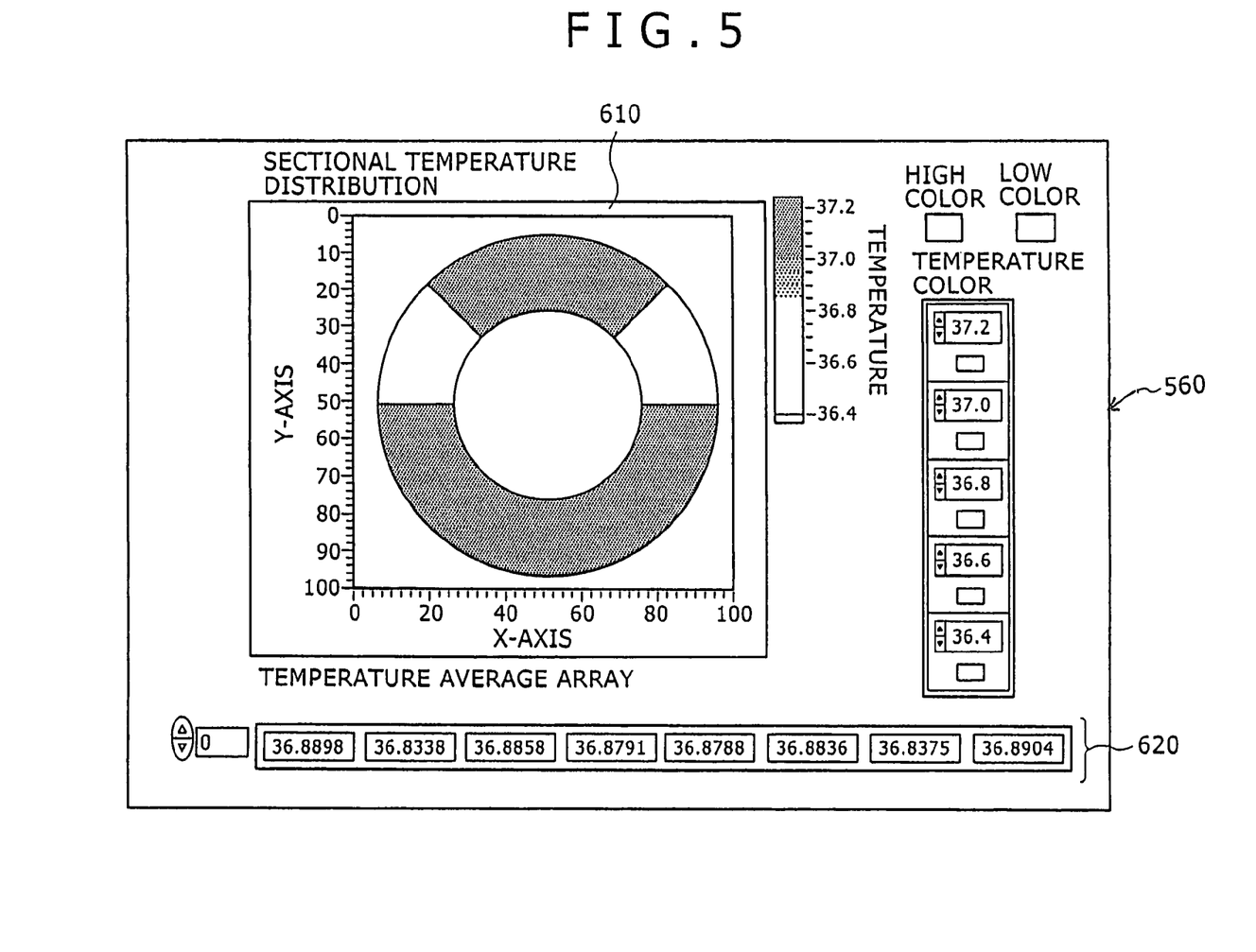
FIG. 5 is a diagram showing a displayed example of a temperature distribution in a blood vessel section.

(1) Pattern Diagram Display:

FIG. 5 shows an example of a displayed temperature distribution of an inner surface of the blood vessel wall. In the displayed example, the temperature distribution represents an average of temperature data in a certain region (angle) of the blood vessel wall. In this example, the region is divided into eight segments. However, the region may be divided into as many segments as desired. In FIG. 5, regions at higher temperatures are indicated by darker colors. Colors that are displayed to indicate different temperatures may be selected by the user. In the displayed examples, the detected temperatures are displayed by not only colors in an area 610, but also numerical values in an area 620 representing average temperatures in the regions for the user to be able to confirm slight temperature differences.

If the temperature of a certain region is so higher than the temperatures of the other regions in the displayed temperature distribution that the temperature difference is of a value indicative of the possibility of the formation of a vulnerable plaque, then the region may be blinked in the displayed image, and information as to the location of that region in the living body of the possible plaque, e.g., the distance, i.e., the length of the guide wire, from the insertion port of the living body may be stored in a memory (not shown) for data accumulation.

Figure 6:
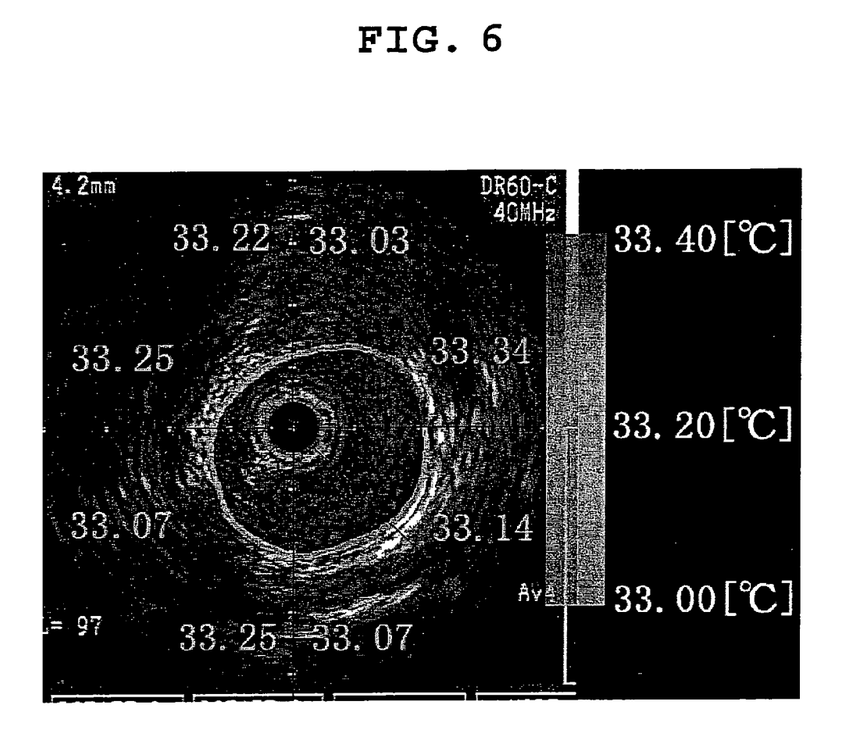
FIG. 6 is a diagram showing a displayed example of an ultrasonic tomographic image and a temperature distribution which are displayed in synchronism with each other.

(2) Tomographic Image and Temperature Diagram Display:

The ultrasonic transverse tomographic image and the temperature distribution may be displayed in separate display areas on the display unit 560. However, they may be synchronized and displayed in a superimposed fashion, as shown in FIG. 6. The ultrasonic transverse tomographic image and the temperature distribution can be synchronized based on a pulse signal from the non-illustrated motor which rotates the imaging core 400. If the motor produces N pulses each time the transducer unit 410 and the temperature sensor 440 make one revolution, then since the transducer unit 410 and the temperature sensor 440 rotate continuously, their signals are measured continuously. The temperature data from the temperature sensor 440 are divided into N data each time the temperature sensor 440 makes one revolution, and averaged M times for the N divided regions. The intravascular temperature distribution is displayed in the N divided regions. The intravascular temperature distribution may be displayed in divided time zones based on the pulse signal.

In FIG. 6, the ultrasonic transverse tomographic image and the temperature distribution are displayed in eight divided regions with the motor rotating at a speed of 30 revolutionsisecond. A ring shown at the center of FIG. 6 represents an afterimage of the ultrasonic catheter, rather than the blood vessel.

As shown in FIG. 6, the ultrasonic transverse tomographic image alone does not show any plaque in the blood vessel. However, when the ultrasonic transverse tomographic image and the temperature distribution are displayed together, they indicate that a small plaque has been formed or will possibly be formed in the near future in a high-temperature region. Since the intravascular temperature is displayed as being high in a region where an arteriosclerotic plaque has possibly been formed, it can be of assistance to the diagnostic process. According to the present embodiment, therefore, it is possible to diagnose plaques that have been difficult to be diagnosed solely with ultrasonic transverse tomographic images, and collect data for preventive medicine.

Figure 7:
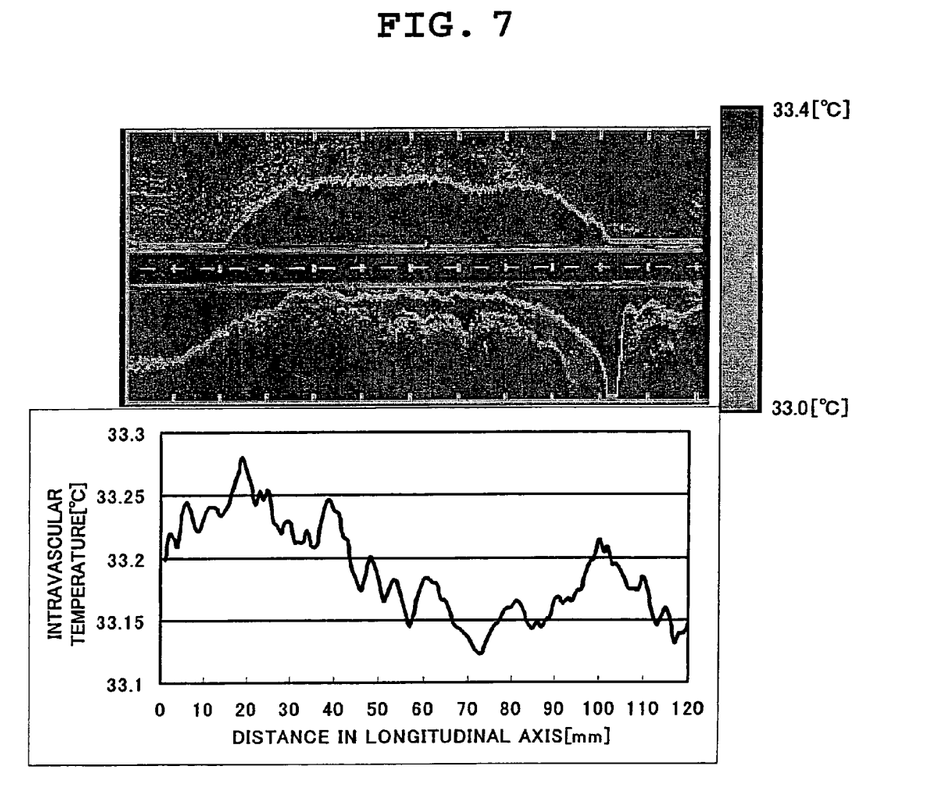
FIG. 7 is a diagram showing a displayed example of an ultrasonic longitudinal tomographic image and a temperature distribution (axial direction)
Figure 8A:
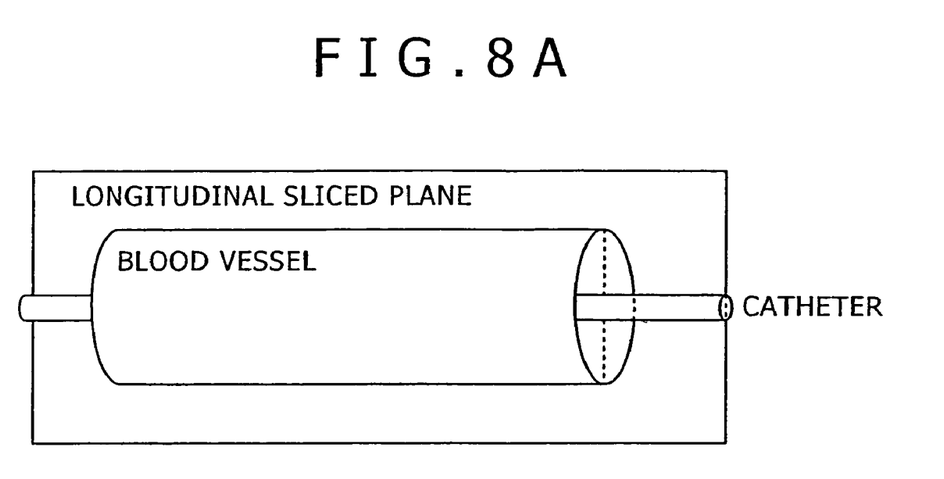
FIGS. 8A and 8B are views illustrative of the concept of the ultrasonic longitudinal tomographic image shown in FIG. 7.
Figure 8B:
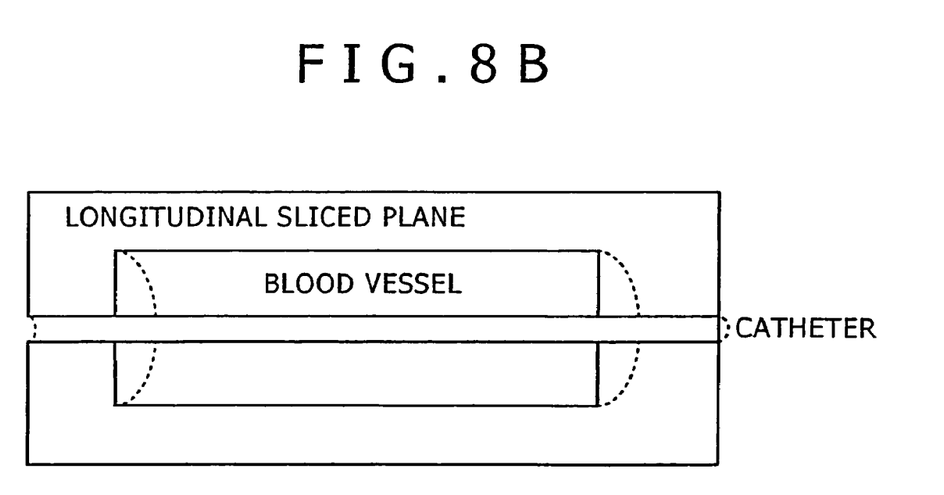

(3) Longitudinal Tomographic Image Display:

Synchronous display of an ultrasonic longitudinal tomographic image and an intravascular longitudinal temperature distribution will be described below with reference to FIGS. 7A and 7B. When the ultrasonic transducer is translated axially at a constant speed in the blood vessel either manually or by a device such as an automatic pull-back motor drive unit or the like which can translate the ultrasonic catheter or the ultrasonic transducer in the ultrasonic catheter at a constant speed back and forth, an ultrasonic longitudinal tomographic image shown in FIG. 7A is displayed on the display unit 560. The ultrasonic longitudinal tomographic image shown in FIG. 7A will be described below. The ultrasonic longitudinal tomographic image shown in FIG. 7A represents a longitudinal tomographic image of the blood vessel as shown in FIG. 8B which is produced by cutting the blood vessel along a longitudinal sliced plane in the scanning direction of the ultrasonic catheter as shown in FIG. 8A. The ultrasonic catheter is indicated by a path shown centrally in FIG. 7A. In FIG. 7A, the blood vessel is shown as having irregular surfaces, where plaques are possibly formed.

An intravascular longitudinal temperature distribution is produced by starting to measure temperature data in synchronism with starting to move the ultrasonic transducer axially in the scanning direction of the ultrasonic catheter and averaging the measured temperature data in a certain period of time.

The intravascular longitudinal temperature distribution is displayed as shown in FIG. 7B. If the intravascular longitudinal temperature distribution is displayed in superimposed relation to the ultrasonic longitudinal tomographic image shown in FIG. 7A, then even when no irregular surfaces are found in the blood vessel, the possibility of the formation of a plaque can be discovered based on the displayed intravascular longitudinal temperature distribution.

(4) Tomographic Image and Longitudinal Tomographic Image Display:

Though not shown, the tomographic image described above in (1) and the longitudinal tomographic image described above in (2) may simultaneously be displayed for a fail-free three-dimensional analysis of the possibility of the formation of a plaque.

Second Embodiment

Figure 9:
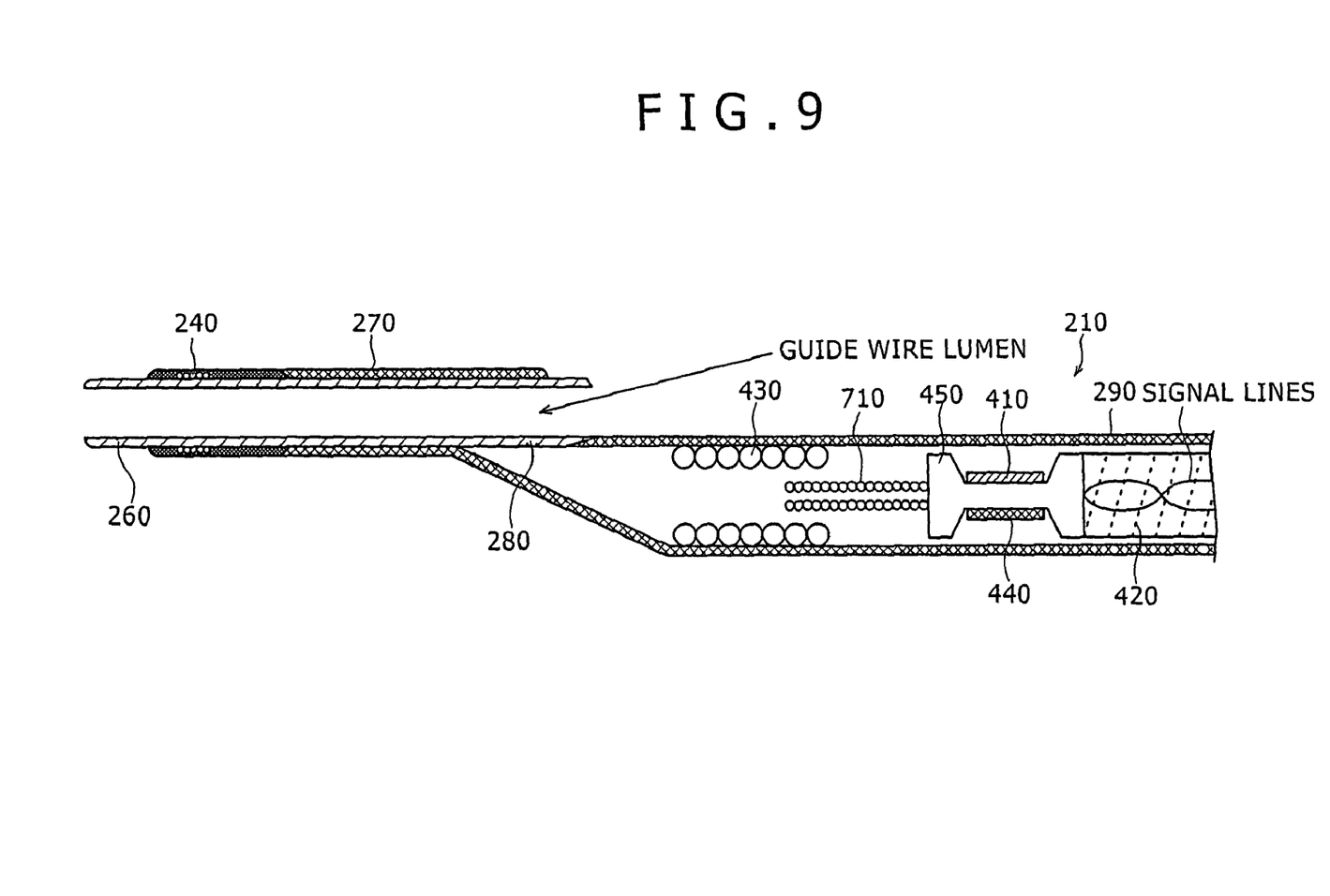
FIG. 9 is a cross-sectional view of a sheath distal end portion according to a second embodiment of the present invention.

FIG. 9 shows in cross section a sheath distal end portion 210 of an ultrasonic catheter according to a second embodiment of the present invention.

The sheath distal end portion 210 shown in FIG. 9 differs from the sheath distal end portion 210 according to the first embodiment shown in FIG. 3 in that a tip end coil 710 is mounted on the housing 450 according to the second embodiment. The tip end coil 710 and the metal coil 430 allow the imaging core 400 to be stably rotated by the non-illustrated motor. Therefore, the metal coil 430 serves as an X-ray marker, prevents the ultrasonic catheter from being bent, and stabilizes the rotation of the imaging core 400.

Other structural and operational details of the ultrasonic catheter according to the second embodiment, and its process of displaying an ultrasonic transverse tomographic image, an ultrasonic longitudinal tomographic image, and a temperature distribution are identical to those of the ultrasonic catheter according to the first embodiment, and will not be described in detail below.

According to the first and second embodiments, as described above, the transducer unit and the temperature sensor, typically a thermistor, are disposed in the distal end portion, or a probe, of the ultrasonic catheter for simultaneously displaying intravascular ultrasonic tomographic and longitudinal tomographic images and an intravascular temperature distribution in blood vessel and plaque regions. The intravascular ultrasonic tomographic and longitudinal tomographic images and the intravascular temperature distribution which are displayed are useful in finding a region where a plaque has been formed and also a region where a plaque will possibly be formed, and making subsequent medical treatment.

The intravascular ultrasonic transverse tomographic image may be divided into differently featured, e.g., differently colored, segments based on information obtained from the temperature data, and the divided segments are displayed. The differently featured segments allow a volume such as a plaque to be easily determined in the tomographic image of the blood vessel.

The intravascular ultrasonic longitudinal tomographic image may be divided into differently featured, e.g., differently colored, segments based on information obtained from the temperature data, and the divided segments are displayed. The differently featured segments allow a volume such as a plaque to be easily determined in the scanning direction of the image core in the blood vessel.

The intravascular ultrasonic transverse tomographic image and the intravascular ultrasonic longitudinal tomographic image allow blood vessel diameters such as intima and middle coat diameters to be measured relatively easily.

Although certain preferred embodiments of the present invention have been shown and described in detail, it should be understood that various changes and modifications may be made therein without departing from the scope of the appended claims.

What is claimed is:

1. An ultrasonic imaging system comprising:
    an insert for being inserted into a blood vessel;
    a drive shaft disposed in said insert;
    an ultrasonic transducer disposed in said insert; and
    at least one temperature sensor disposed in said insert;
    wherein said transducer and said at least one temperature sensor are arranged to scan the blood vessel in a direction which is perpendicular and parallel to a longitudinal axis of the blood vessel, wherein said transducer is operable to provide a tomographic image of the blood vessel, and one of said at least one temperature sensor is a thermistor and is operable to measure an intravascular temperature distribution in the blood vessel, and wherein said thermistor and said transducer are mounted at opposite sides of a single housing which is fixed at a distal portion of said drive shaft so that said thermistor is disposed in the same position as said transducer in a longitudinal direction of said insert.

2. The ultrasonic system according to claim 1, wherein said transducer has a front side which sends and/or receives an ultrasonic signal, and a rear side, and said at least one temperature sensor is mounted opposite the rear side of said transducer.

3. A diagnostic imaging system comprising:
    an ultrasonic catheter having an insert for being inserted into a blood vessel, a drive shaft disposed in said insert, a transducer disposed in said insert, and at least one temperature sensor disposed in said insert, wherein one of said at least one temperature sensor is a thermistor and said thermistor and said transducer are mounted at opposite sides of a single housing which is fixed at a distal portion of said drive shaft so that said thermistor is disposed in the same position as said transducer in a longitudinal direction of said insert; and
    a diagnostic imaging apparatus having an ultrasonic signal receiver for receiving an ultrasonic signal from said transducer, a temperature signal receiver for receiving an intravascular temperature signal from said at least one temperature sensor, and an image constructing unit for constructing an image from a tomographic vascular image generated from said ultrasonic signal and intravascular temperature information generated from said intravascular temperature signal, in relation to positional information of said ultrasonic signal and said intravascular temperature signal.

4. The diagnostic imaging system according to claim 3, the diagnostic imaging apparatus further comprising:
    a display unit for displaying said intravascular temperature information divided in differently colored segments, together with said tomographic vascular image.

5. The diagnostic imaging apparatus according to claim 4, wherein said display unit is operable to display said intravascular ultrasonic longitudinal tomographic image and said intravascular longitudinal temperature information in superimposed relation to each other.

6. The diagnostic imaging system according to claim 3, wherein said display unit is operable to display a pattern diagram of the blood vessel having a plurality of divided regions with an average value of said intravascular temperature information in association with each of said divided regions.

7. The diagnostic imaging system according to claim 3, wherein said display unit is operable to display the intravascular temperature information and said tomographic vascular image in superimposed relation to each other.

8. The diagnostic imaging system according to claim 3, wherein said insert, together with said at least one temperature sensor and said transducer is arranged to be translated along a longitudinal axis of the blood vessel at a constant speed, and said ultrasonic signal receiver and said temperature signal receiver are operable to receive an ultrasonic signal representative of an intravascular ultrasonic longitudinal tomographic image and an intravascular temperature signal representative of intravascular longitudinal temperature information, respectively, while said at least one temperature sensor and said transducer are being moved, and wherein said display unit is operable to simultaneously display said intravascular ultrasonic longitudinal tomographic image and said intravascular longitudinal temperature information in synchronism with the movement of said at least one temperature sensor and said transducer.

9. An ultrasonic imaging method comprising the steps of:
A. inserting into a blood vessel an insert containing a drive shaft, an ultrasonic transducer and at least one temperature sensor, wherein one of said at least one temperature sensor is a thermistor and said thermistor and said transducer are mounted at opposite sides of a single housing which is fixed at a distal portion of said drive shaft so that said thermistor is disposed in the same position as said transducer in a longitudinal direction of said insert; and
B. causing said transducer and said at least one temperature sensor to scan the blood vessel in a direction which is perpendicular and parallel to a longitudinal axis of the blood vessel, wherein said transducer provides a tomographical image of the blood vessel, and said at least one temperature sensor measures an intravascular temperature distribution in the blood vessel, said transducer and said at least one temperature sensor simultaneously scanning the blood vessel from the same position with reference to the longitudinal direction of the blood vessel.

10. The method according to claim 9 wherein during step B said transducer scans in a first direction, and said at least one temperature sensor scans in a second direction opposite said first direction.

11. A diagnostic imaging method comprising the steps of:
A. inserting into a blood vessel an insert containing a drive shaft, an ultrasonic transducer and at least one temperature sensor, wherein one of said at least one temperature sensor is a thermistor and said thermistor and said transducer are mounted at opposite sides of a single housing which is fixed at a distal portion of said drive shaft so that said thermistor is disposed in the same position as said transducer in a longitudinal direction of said insert;
B. causing said transducer and said at least one temperature sensor to scan the blood vessel, said transducer and said at least one temperature sensor simultaneously scanning the blood vessel from the same position with reference to the longitudinal direction of the blood vessel;
C. supplying to an ultrasonic signal receiver of a diagnostic imaging apparatus an ultrasonic signal from said transducer;
D. supplying to a temperature signal receiver of said diagnostic imaging apparatus an intravascular temperature signal from said at least one temperature sensor;
E. supplying said ultrasonic signal and said intravascular temperature signal to an imaging constructing unit of said diagnostic imaging apparatus for constructing an image based upon a tomographic vascular image generated from said ultrasonic signal, and intravascular temperature information generated from said intravascular temperature signal, in relation to positional information of said ultrasonic signal and said intravascular temperature signal; and
F. displaying said image on a display unit.

12. The method according to claim 11 wherein step F comprises displaying said intravascular temperature information divided in differently colored segments.

13. The method according to claim 12 wherein during step F said display unit displays said intravascular ultrasonic longitudinal tomographic image and said intravascular longitudinal temperature information in superimposed relation to each other.

14. The method according to claim 11 wherein during step F said display unit displays a pattern diagram of the blood vessel having a plurality of divided regions with an average value of said intravascular temperature information in association with each of said divided regions.

15. The method according to claim 11 wherein during step F said display unit displays the intravascular temperature information and said tomographic vascular image in superimposed relation to each other.

16. The method according to claim 11 wherein during step B said insert, together with said at least one temperature sensor and said transducer, is translated along a longitudinal axis of the blood vessel at a constant speed; during step C said ultrasonic signal receiver receives an ultrasonic signal representative of an intravascular ultrasonic longitudinal tomographic image as said transducer is being translated; during step D said temperature signal receives an intravascular temperature signal representative of intravascular longitudinal temperature information as said at least one temperature sensor is being translated; and during step F said display unit simultaneously displays said intravascular ultrasonic longitudinal tomographic image and said intravascular longitudinal temperature information in synchronism with the translation of said at least one temperature sensor and said transducer.

* * * * *